（12）United States Patent
Nashida et al.

(10) Patent No.: US 11,191,468 B2
(45) Date of Patent: Dec. 7, 2021

(54) VEHICULAR NOTIFICATION APPARATUS

(71) Applicant: DENSO CORPORATION, Kariya (JP)

(72) Inventors: Junya Nashida, Kariya (JP); Ichiro Yoshida, Kariya (JP)

(73) Assignee: DENSO CORPORATION, Kariya (JP)

( * ) Notice: Subject to any disclaimer, the term of this patent is extended or adjusted under 35 U.S.C. 154(b) by 282 days.

(21) Appl. No.: 16/566,482

(22) Filed: Sep. 10, 2019

(65) Prior Publication Data

US 2020/0000392 A1  Jan. 2, 2020

Related U.S. Application Data

(63) Continuation of application No. PCT/JP2018/004213, filed on Feb. 7, 2018.

(30) Foreign Application Priority Data

Apr. 11, 2017 (JP) .............................. JP2017-078228

(51) Int. Cl.
A61B 5/18 (2006.01)
G06F 3/01 (2006.01)
A61B 5/369 (2021.01)
G01C 21/34 (2006.01)
G01C 21/36 (2006.01)

(52) U.S. Cl.
CPC ................ A61B 5/18 (2013.01); A61B 5/369 (2021.01); G06F 3/013 (2013.01); G06F 3/015 (2013.01); G01C 21/3415 (2013.01); G01C 21/3629 (2013.01); G06F 2203/011 (2013.01)

(58) Field of Classification Search
CPC ..... G08G 1/16; G06F 2203/011; G06F 3/015; G06F 3/013; G01C 21/3641; G01C 21/3629; G01C 21/3415; A61B 5/369; A61B 5/18; A61B 5/165; A61B 5/163
See application file for complete search history.

(56) References Cited

U.S. PATENT DOCUMENTS

| 8,565,820 | B2* | 10/2013 | Riemer | H04M 1/67 455/557 |
| 8,922,376 | B2* | 12/2014 | Kangas | H04M 1/72454 340/573.1 |
| 9,465,978 | B2* | 10/2016 | Hachisuka | A61B 5/165 |
| 10,981,575 | B2* | 4/2021 | Kang | B60G 17/019 |
| 2015/0078632 | A1 | 3/2015 | Hachisuka et al. | |
| 2015/0211868 | A1 | 7/2015 | Matsushita et al. | |
| 2017/0291544 | A1* | 10/2017 | Ishihara | B60K 37/06 |
| 2018/0173230 | A1* | 6/2018 | Goldman-Shenhar | B60W 50/08 |
| 2019/0061772 | A1* | 2/2019 | Prinz | A61B 5/18 |

FOREIGN PATENT DOCUMENTS

| JP | 2003339681 A | 12/2003 |
| JP | 2006092129 A | 4/2006 |
| JP | 2010038821 A | 2/2010 |

(Continued)

Primary Examiner — Mihir K Rayan
(74) Attorney, Agent, or Firm — Harness, Dickey & Pierce, P.L.C.

(57) ABSTRACT

A vehicular notification apparatus detects an emotion of a driver based on a line-of-sight detection result and a brain activity detection result, and performs control to suppress notification in response to that the detected emotion of the driver is uncomfortable.

6 Claims, 10 Drawing Sheets

(56) References Cited

FOREIGN PATENT DOCUMENTS

| | | | |
|---|---|---|---|
| JP | 2013216241 | A | 10/2013 |
| JP | 201749629 | A | 3/2017 |
| WO | WO-2013/111409 | A1 | 8/2013 |
| WO | WO-2014/013985 | A1 | 1/2014 |

\* cited by examiner (a) | (^_^) | COMFORTABLE (b) | (·_·) | NORMAL (c) | (=_=;) | UNCOMFORTABLE

VEHICULAR NOTIFICATION APPARATUS

CROSS REFERENCE TO RELATED APPLICATIONS

The present application is a continuation application of International Patent Application No. PCT/JP2018/004213 filed on Feb. 7, 2018, which designated the U.S. and claims the benefit of priority from Japanese Patent Application No. 2017-78228 filed on Apr. 11, 2017. The entire disclosures of all of the above applications are incorporated herein by reference.

TECHNICAL FIELD

The present disclosure relates to a vehicular notification apparatus that outputs audio guidance.

BACKGROUND

In some navigation apparatuses performing a route guidance, if a vehicle deviates from the guidance route, an audio guidance is outputted such as "deviated from the route, perform re-route calculation". However, the driver may intentionally select a different route that is deviated from the guidance route (that is, a route that is incorrect when viewed from the navigation apparatus). In such a case, the driver feels bothersome or uncomfortable if the audio guidance is repeated.

SUMMARY

According to an embodiment of the present disclosure, a vehicular notification apparatus detects an emotion of a driver based on a line-of-sight detection result and a brain activity detection result, and performs control to suppress notification in response to that the detected emotion of the driver is uncomfortable.

BRIEF DESCRIPTION OF DRAWINGS

The above and other objects, features and advantages of the present disclosure will become more apparent from the following detailed description made with reference to the accompanying drawings. In the drawings.

DETAILED DESCRIPTION

First Embodiment

Figure 1:
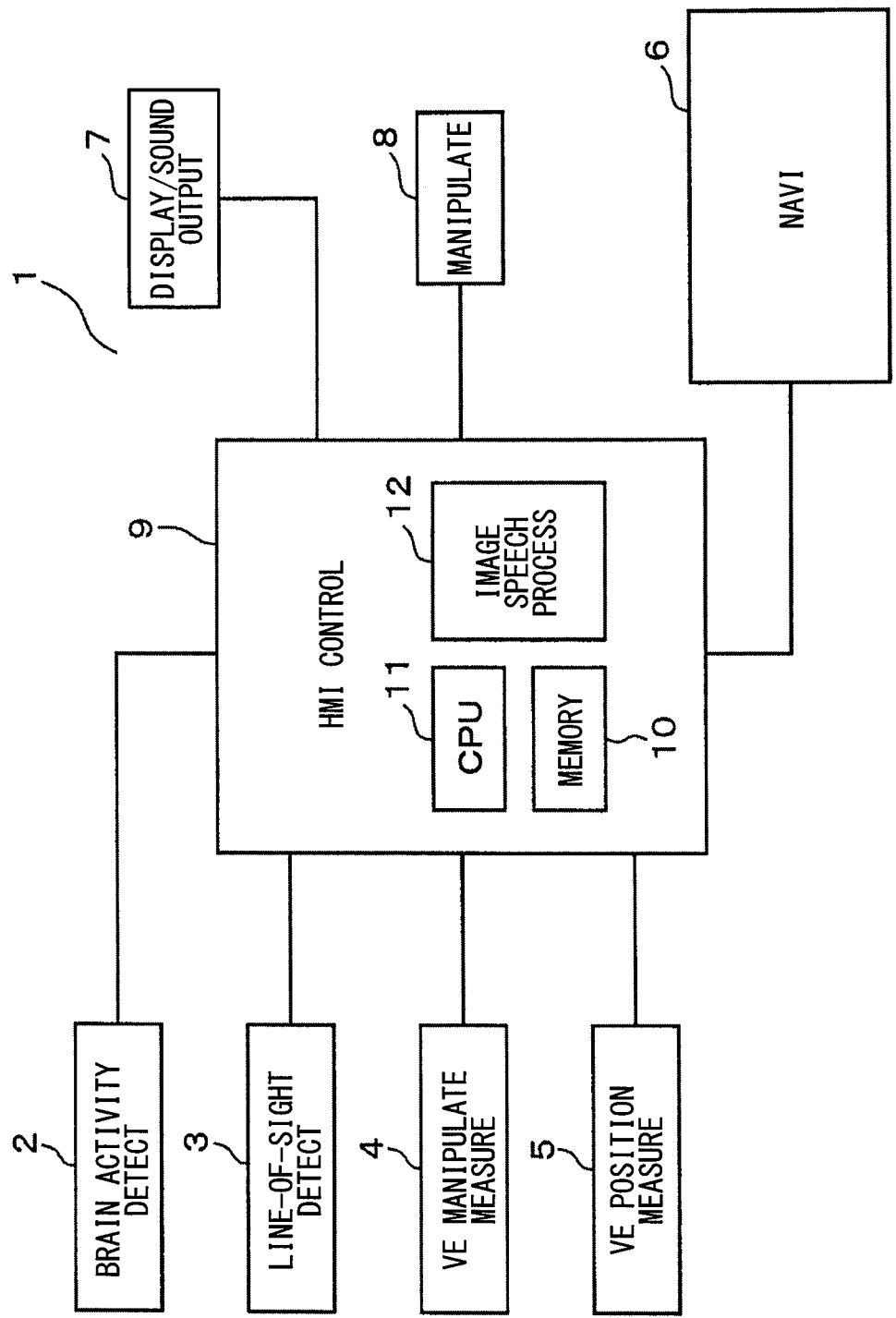
FIG. 1 is a block diagram of a vehicle notification apparatus according to a first embodiment.

The following will describe a first embodiment of the present disclosure with reference to FIGS. 1 to 12. As shown in FIG. 1, a vehicular notification apparatus 1 of the present embodiment includes a brain activity detection unit 2 (which may be also referred to as a brain activity detector), a line-of-sight detection unit 3 (which may be also referred to as a line-of-sight detector), a vehicle manipulation measurement unit 4 (which may be also referred to as a vehicle manipulation detector), a vehicle position measurement unit 5 (which may be also referred to as a vehicle position detector), and a navigation unit 6 (which may be also referred to as a navigation device), a display and sound output unit 7 (which may be also referred to as a notification device), a manipulation unit 8 (which may be also referred to as a manipulation device), and an HMI (Human Machine Interface) controller 9 (which may be also referred to simply as a controller). The HMI controller 9 is connected with the forgoing units 2 to 8 via an in-vehicle local area network (i.e., a signal link or a communication link), as shown in FIG. 1.

The brain activity detection unit 2 includes a plurality of sensors (for example, an electroencephalogram sensor etc.) which are attached closely to several positions of the brain of the driver for measuring the activity of several regions of the brain of the driver (i.e., user) by using light, electromagnetic waves, etc. Then, the brain activity detection unit 2 transmits the brain activity measurement signal (that is, brain activity data) to the HMI controller 9.

The HMI controller 9 may be a controller configured by including (i) hardware circuits (circuitry), or (ii) a microcomputer, or (iii) a combination of the hardware circuits and the microcomputer, to thereby provide a plurality of functions. As one example of the present embodiment, the HMI controller 9 is described as being a microcomputer.

The HMI controller 9 determines, based on the received brain activity measurement signal, the driver's emotion, a positive or negative awareness, or the presence or absence of awareness of failure. In this case, data on the correlation between the activity (i.e., the excited area) of each part of the brain and emotion is recorded in a brain activity database provided in a memory 10 in the HMI controller 9. The HMI controller 9 sequentially stores to accumulate information such as the driver's emotion and various awareness determined as described above, that is, information obtained by detecting the change in driver's brain activity almost in real time. The memory 10, which is configured of, for example, a ROM, a RAM, a flash memory, a hard disk, etc., stores a control program and various data. The HMI controller 9 includes, in addition to the memory 10, a CPU 11 for controlling the entire HMI controller 9, and an image and audio processing unit 12 for generating image information to be displayed, audio information to be outputted, and the like.

In addition, the brain activity detection unit 2 includes an interface (for example, a communication unit) for transmitting the measured brain activity measurement signal to an external device. In addition, the brain activity detection unit 2 is configured to be able to specify a specific brain region of the driver and measure brain activity of the specific brain region according to an external instruction.

The line-of-sight detection unit 3 includes an image capturing unit (for example, a camera) to have a function for capturing an image of the upper body of the driver, the driver's eye movement (for example, gaze or line of sight), the driver's expression, and the driver's speech (for example, mouth movement), to obtain the driver's behavior by acquiring line-of-sight direction data, facial expression data, and mouth movement data. In addition, whether the driver speaks or not is determined in combination with a microphone (not shown) in a vehicle compartment. For example, when it is determined that the driver has moved their line of sight into the vehicle compartment, it is determined which in-vehicle device the driver has seen by referring to a database recording the layout of various in-vehicle devices in the vehicle compartment. Then, the line-of-sight detection unit 3 transmits data of the line-of-sight direction, data of the expression, and data of the movement of the mouth to the HMI controller 9.

The line-of-sight detection unit 3 also has an interface for transmitting data of a line-of-sight direction, data of an expression, data of movement of a mouth, and the like to an external device. Furthermore, the line-of-sight detection unit 3 is configured to be able to detect how a driver's line-of-sight movement or the like is performed by designating a specific point of time by an external instruction. Further, in the present embodiment, after a speech notification is performed, what line-of-sight movement the driver has performed is measured to determine whether the speech notification is recognized by the driver. Further, suppose a case that the driver feels that the navigation unit 6 has given an alarm of "deviated from the route, perform re-route calculation (i.e., re-search)", too many times. In the present embodiment, in such a case, according to the detection of the driver's line of sight, the notification is provided only when the driver "looks away and misses the guidance route", that is, only when the notification is necessary.

The vehicle manipulation measurement unit 4 measures (i) the driver's manipulations for various in-vehicle devices in the driver's vehicle driving and (ii) the operations of those various in-vehicle devices. The various in-vehicle devices involved in the driver's vehicle driving, include, for example, steering, brake, accelerator, gear, and switches of various in-vehicle devices. In addition, when a brought-in device (for example, a smartphone, a mobile phone, a tablet, etc.) is connected to the vehicle, it is possible to measure the presence or absence of a manipulation or an operation of the brought-in device. Then, the vehicle manipulation measurement unit 4 transmits various data related to the measured manipulation of the vehicle to the HMI controller 9. Further, the vehicle manipulation measurement unit 4 includes an interface for transmitting various data related to the manipulation of the vehicle to an external device.

The vehicle position measurement unit 5 includes (i) a function of measuring a current position of the vehicle using a position measurement unit such as a GPS receiver, and (ii) a function of measuring a current time and various elapsed times (that is, a function of a timer unit). The vehicle position measurement unit 5 can measure the traveling speed of the vehicle by measuring position information of the vehicle and the elapsed time. Then, the vehicle position measurement unit 5 transmits the measured position information, information on elapsed time, and the like to the HMI controller 9. In addition, the vehicle position measurement unit 5 includes an interface for transmitting the measured position information, information on elapsed time, and the like to an external device.

The present embodiment is provided with the following two determinations when the driver is notified by speech (i.e., the driver receives a notification of speech information). That is, whether or not the driver's brain activity (e.g., emotion) changes by a threshold value or more due to the notification is determined by the brain activity detection unit 2; and what kind of effect the notification of voice information gives the driver is determined by the line-of-sight detection unit 3. Also, if that the driver's emotion has changed due to the notification of voice information is detected by the brain activity detection unit 2, the occurrence of the change in driver's emotion is recorded in connection with the notification of speech information. Also, the brain activity with respect to the degree of the driver's recognition against the notification of speech information is measured by the brain activity detection unit 2; the measurement result is recorded.

The navigation unit 6 includes functions as a route information storage unit, a route calculation unit, and a travel route suitability determination unit. The route calculation unit calculates a travel route from an inputted departure point and a destination point. The route information storage unit stores the calculated travel route. The traveling route suitability determination unit determines (i.e., map matching) on which point of a road on the map the route that the vehicle is traveling, and determines the matching status between the calculated travel route and the actual travel route of the vehicle. Then, when the vehicle deviates from the calculated travel route, the route calculation unit recalculates (that is, re-searches) the travel route to the destination and stores it in the route information storage unit.

Also, in the present embodiment, when it is determined that the vehicle travels on a road that has deviated from the calculated travel route, speech guidance is usually performed to notify the user that the vehicle has deviated from the route. In particular, in the present embodiment, when the driver intentionally deviates from a route, it is determined whether or not speech guidance (i.e., notification) is required, and notification is performed only when necessary. The specific control will be described later.

The display and sound output unit 7 executes control to display an image on a display or to output sound or speech from a speaker when the HMI controller 9 has information to be notified to the driver (i.e., user). The manipulation unit 8 is a device for receiving a driver's input manipulation and the like, and is configured by manual manipulation devices such as a button, a lever, a switch, and a touch panel. The display and sound output unit 7 has a function as a notification unit.

The HMI controller 9 causes the line-of-sight detection unit 3 to measure the situation of the line-of-sight direction of the driver when the brain activity detection unit 2 detects the movement of the driver's emotion at the point of time when the driver receives notification information. As a result, when it is determined that the driver does not need the notification information or that the driver cannot recognize the notification information, the series of driver's action records are stored in the memory 10 as driver status information (that is, user status information) of the day.

In the present embodiment, the HMI controller 9 can determine in a short time whether or not the driver needs notification information based on the driver's action (i.e. driving manipulation etc.) and brain activity on that day, thereby enabling the execution of a notification operation that matches the state of the driver.

Further, in the present embodiment, the driver can be inquired directly about the cause of why the driver's emotional movement has occurred. That is, first the HMI controller 9 confirms that the driver is in a normal state (that is, the cool state) using the brain activity detection unit 2 after a predetermined period of time has elapsed since the occurrence of an event that needs to be notified to the driver. When confirming such a normal state, an inquiry screen is displayed on the display by the display and sound output unit 7 so that the driver can be inquired directly about the cause of why the driver's emotional movement has occurred. In this configuration, the HMI controller 9 can grasp the usability of the driver's equipment by the driver answering the inquiry. Further, the HMI controller 9 grasps the driver's straying in manipulation and the degree of dependence on the in-vehicle device from the line-of-sight detection result by the line-of-sight detection unit 3 and the brain activity measurement result by the brain activity detection unit 2. (i) The frequency of notification and/or (ii) information content data can thus be appropriately selected and set according to the driver's state.

Figure 10:
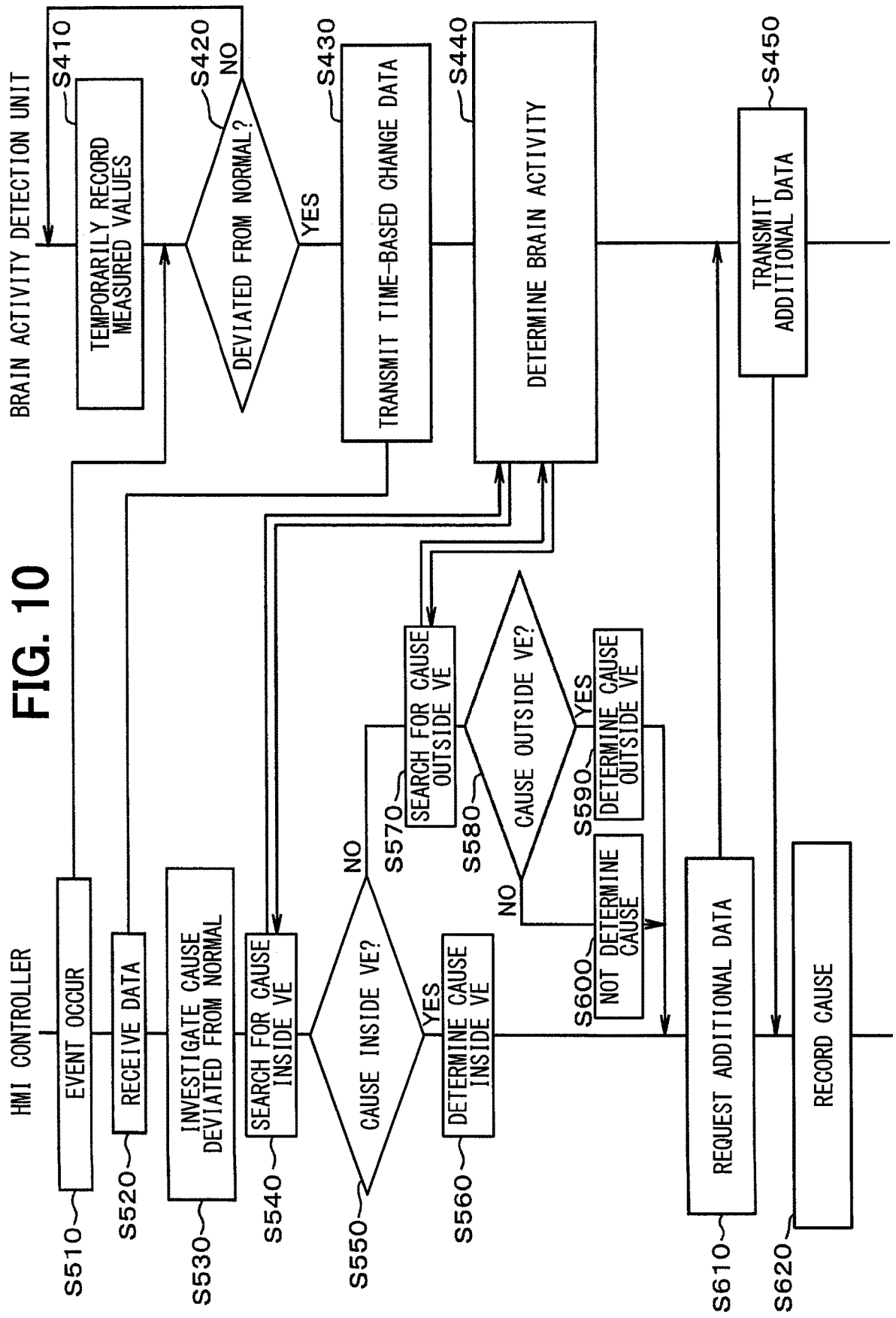
FIG. 10 is a sequence diagram of control of an HMI controller and a brain activity detection unit.

The following will describe flowcharts of FIGS. 2 to 5 executed by the HMI controller 9 and a sequence diagram of FIG. 10 executed by the HMI controller 9 and the brain activity detection unit 2. The respective flowcharts and the sequence diagram include sections, e.g., each represented as S10, S20, or the like.

First, a main control of the intention determination and a notification control by the HMI controller 9 will be described with reference to the flowchart of FIG. 2. In S10 of FIG. 2, the HMI controller 9 measures the current position of the vehicle, that is, receives the information of the current position of the vehicle measured by the vehicle position measurement unit 5. Subsequently, the process proceeds to S20, where the HMI controller 9 determines whether the notification location and the notification timing have come.

Here, when the notification location and the notification timing have not come (NO), the process returns to S10. In S20, when the notification location and the notification timing have come (YES), the process proceeds to S30. In S30, the HMI controller 9 executes each process of the driver's looking-away determination and the driver's unawareness determination based on the line-of-sight detection result by the line-of-sight detection unit 3 and the brain activity detection result by the brain activity detection unit 2. The specific control of the driver's looking-away determination and the driver's unawareness determination will be described later.

Subsequently, the process proceeds to S40. In S40, the HMI controller 9 determines whether the notification condition requiring notification is satisfied or not, based on the determination result of the driver's looking-away determination and the driver's unawareness determination. Here, when the notification condition is not satisfied (NO), the process returns to S10. When the notification condition is satisfied in S40 (YES), the process proceeds to S50, where the HMI controller 9 transmits the notification information to the display and sound output unit 7. The notification operation is performed by the display and sound output unit 7, that is, a notification message is displayed on a display (for example, a display provided on the instrument panel) or notification speech information is outputted or announced from the speaker.

Subsequently, the process proceeds to S60, where the HMI controller 9 measures the effect of the notification operation. Here, it is measured how the driver's emotion has changed by notification, and the details will be described later. Thereafter, the process proceeds to S70, where the HMI controller 9 changes the notification condition based on the measurement result of the effect of the above-described notification operation. In this case, if the driver's feeling is comfortable after the notification operation is performed, the notification condition is determined to be appropriate, and thus the notification condition is not amended. In contrast, when the driver feels uncomfortable by the notification, the cause of being uncomfortable (i.e., the cause of the discomfort) is clarified and the notification condition is changed. The process then returns to S10, and the above-described process is repeatedly executed.

Next, the control of S30 of FIG. 2, that is, the specific control of the driver's looking-away determination and the driver's unawareness determination will be described with reference to the flowchart of FIG. 3. First, in S110 of FIG. 3, the line-of-sight detection unit 3 measures the direction of the line of sight of the driver in order to see an object such as a device in the vehicle or a road outside the vehicle or another traveling vehicle; the HMI controller 9 receives the measurement result. In this case, the line-of-sight detection unit 3 measures, for example, the vertical and horizontal angles of the line of sight of the driver with respect to the traveling direction of the vehicle.

Based on the measurement result, the HMI controller 9 roughly grasps what the driver's line of sight is pointing to. For example, it is determined that the driver is looking at an area outside of the vehicle if the driver's line of sight is within an angle range of the windshield glass. Further, whether the driver looks at an object carefully or unintentionally is determined based on the movement (for example, time-based change) of the angle of the driver's line of sight. That is, it is determined based on the difference between the time-based change of the line-of-sight direction angle when a target object is followed certainly by the line of sight and the time-based change of the line-of-sight direction angle when it is followed unintentionally by the line of sight. If an object to be looked at is present, there is a change in the line-of-sight direction angle according to the speed of the vehicle. In addition, if the driver looks around unstably, a plurality of objects to be looked at are present; after looking at any of them for a certain period of time, an action for looking at the next object is performed. Such an action can also be determined by measuring the time-based change of the driver's line-of-sight direction.

Subsequently, the process proceeds to S120, where the HMI controller 9 determines whether or not the driver's line-of-sight detection result is abnormal (for example, whether the driver looks around unstably or not). When the driver's line-of-sight detection result is abnormal (for example, when the driver looks around unstably), the process proceeds to S130. In S130, the brain activity detection unit 2 measures the brain activity of the driver, and the HMI controller 9 receives the measurement result.

Then, the process proceeds to S140, where the HMI controller 9 determines whether the driver feels anxious based on the measurement result of the brain activity. Here, if the driver feels anxious (YES), the process proceeds to S150. In S150, the HMI controller 9 prepares data for determining to execute notification since the driver is in a state of anxiety. As a result, the present control is ended, and the process shifts to S50 in FIG. 2.

Further, if the driver does not feel anxious at S140 (NO), the process proceeds to S160, where the HMI controller 9 prepares data for determining not to execute notification. As a result, the present control is ended, and the process shifts to S50 in FIG. 2.

Further, in S120, when there is no abnormality in the line-of-sight detection result (for example, when the driver is not looking around unstably) (NO), the process proceeds to S160, where the HMI controller 9 prepares data for determining not to execute notification. Then, the control ends.

Figure 2:
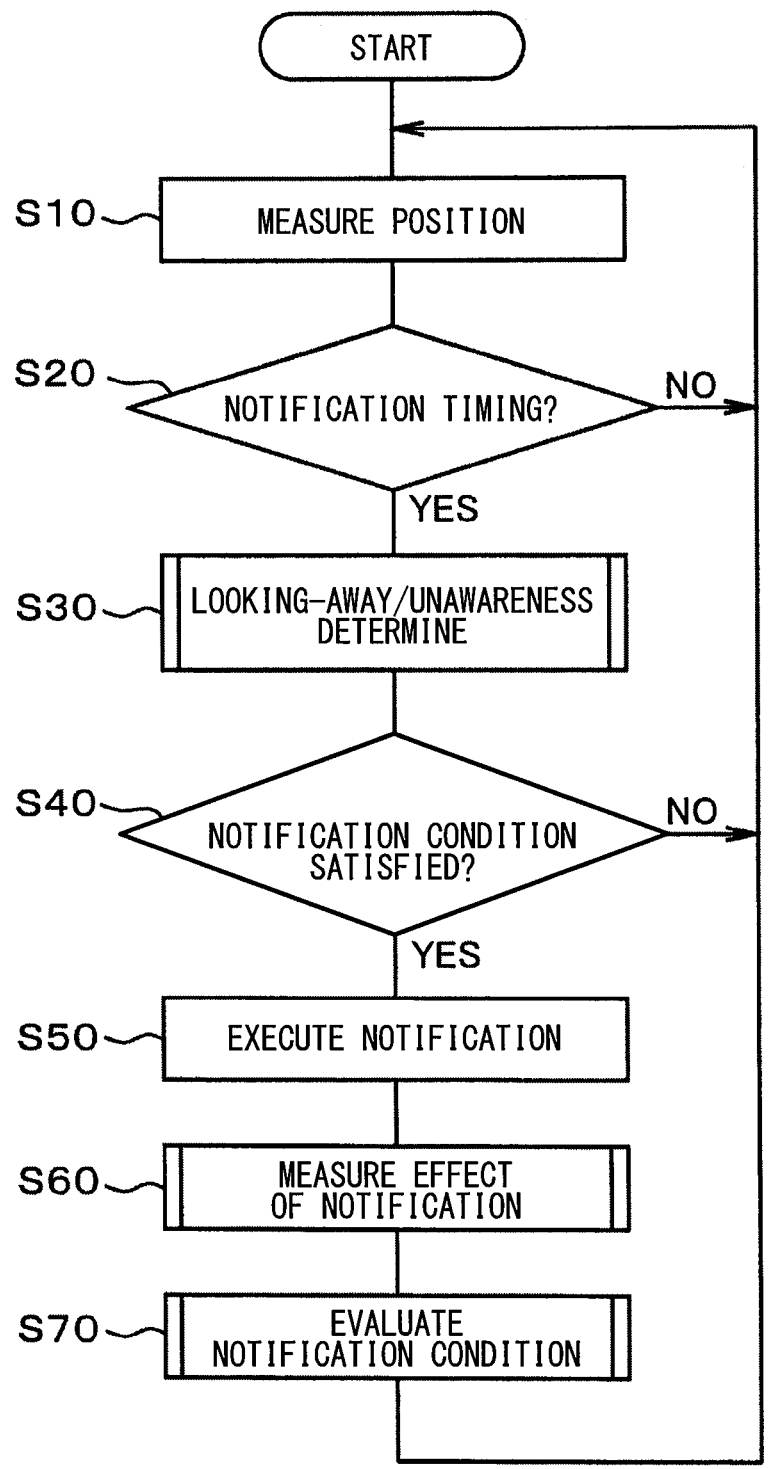
FIG. 2 is a flowchart of a main control of an HMI controller.
Figure 3:
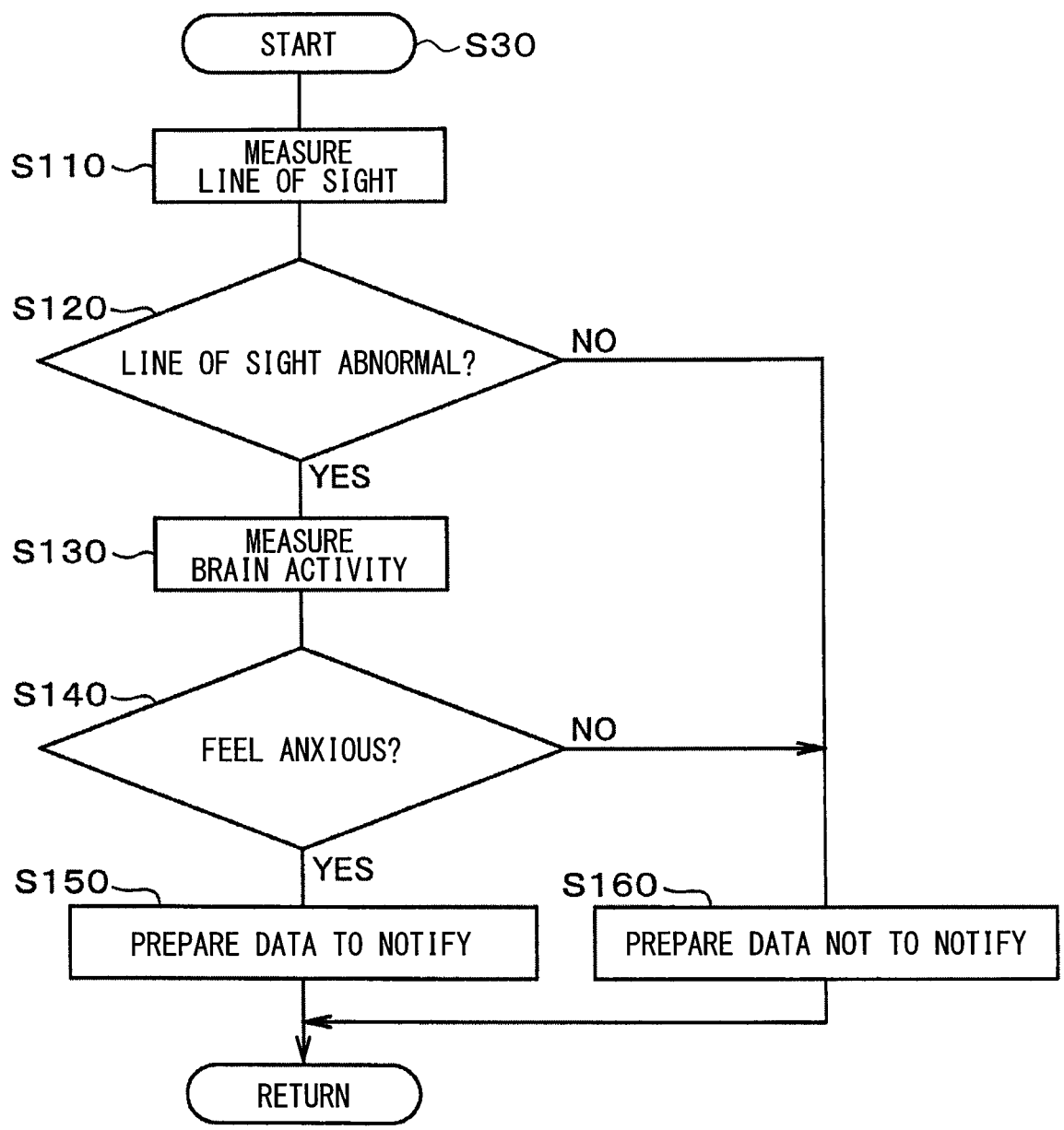
FIG. 3 is a flowchart of controls of determination of driver's looking away and determination of driver's unawareness.
Figure 4:
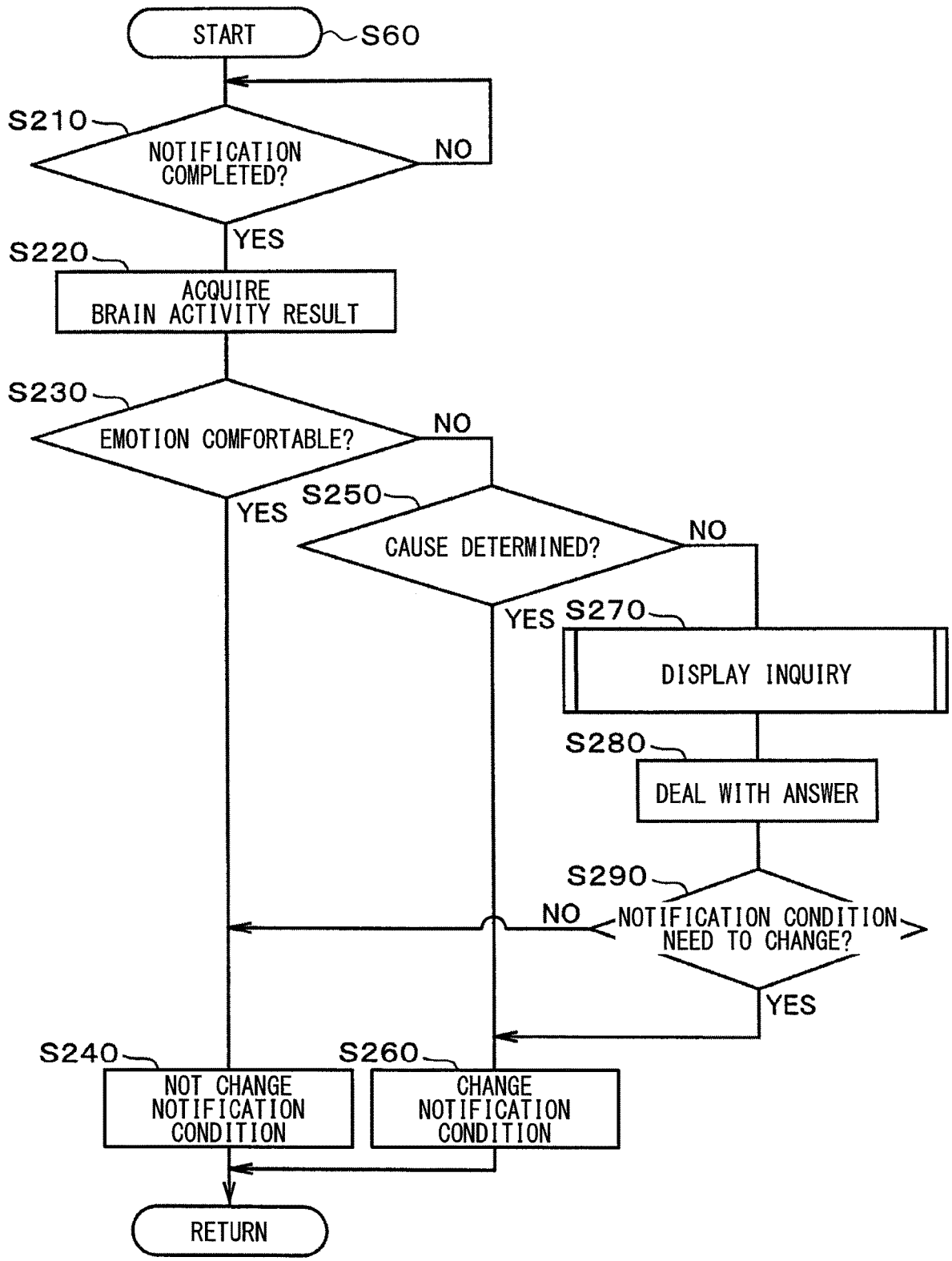
FIG. 4 is a flowchart of control of measurement of effects of notification operation.

The following will describe a control of S60 of FIG. 2, i.e., a specific control of measurement of the effect of the notification operation with reference to the flowchart of FIG. 4. First, in S210 of FIG. 4, the HMI controller 9 determines whether the notification operation is completed. Here, when the notification operation is not completed (NO), the process returns to S210.

In S210, when the notification operation is completed (YES), the process proceeds to S220. In S220, the HMI controller 9 receives the measurement result of measuring the brain activity of the driver from the brain activity detection unit 2. Subsequently, the process proceeds to S230, where the HMI controller 9 determines whether the driver's emotion is comfortable based on the measurement result of the brain activity. Here, when the driver's emotion is comfortable (YES), the process proceeds to S240, where the HMI controller 9 sets data so as not to change the notification condition. As a result, the present control is ended, and the process proceeds to S70 of FIG. 2.

In S230, when the driver's emotion is not comfortable (NO), the process proceeds to S250. In S250, the HMI controller 9 determines whether the cause of the driver's emotion being uncomfortable is clear or determined based on various information from the brain activity detection unit 2, the line-of-sight detection unit 3, the vehicle manipulation measurement unit 4, the vehicle position measurement unit 5, and the navigation unit 6. For example, when there is a driving manipulation such as a sharp steering of the wheel or a sudden braking, the driving manipulation can be clearly determined or identified as the cause of being uncomfortable (discomfort) in the driver's emotion. In S250, when the cause of discomfort in the driver's emotion is determined (YES), the process proceeds to S260, where the HMI controller 9 sets data to change the notification condition. As a result, the present control is ended, and the process proceeds to S70 of FIG. 2.

When the cause of discomfort in the driver's emotion is not determined at S250 (NO), the process proceeds to S270. In S270, the HMI controller 9 performs processing for inquiring the driver of the cause of discomfort in the emotion by displaying an inquiry screen under the condition that does not affect the driving manipulation (for example, during a period of time in which a response input can be manipulated safely such as a period of time of traffic signal waiting). The inquiry screen preferably displays options that the driver can easily select. The specific control of the process for inquiring the driver of the cause of discomfort in the emotion will be described later.

Subsequently, the process proceeds to S280, where the HMI controller 9 deals with an answer from the driver. Then, the process proceeds to S290, where the HMI controller 9 determines whether the change of the notification condition is necessary. Here, if the change of the notification condition is not necessary (NO), the process proceeds to S240, where the notification condition is not changed. In contrast, when it is determined in S290 that the notification condition needs to be changed (YES), the process proceeds to S260 to change the notification condition.

Figure 5:
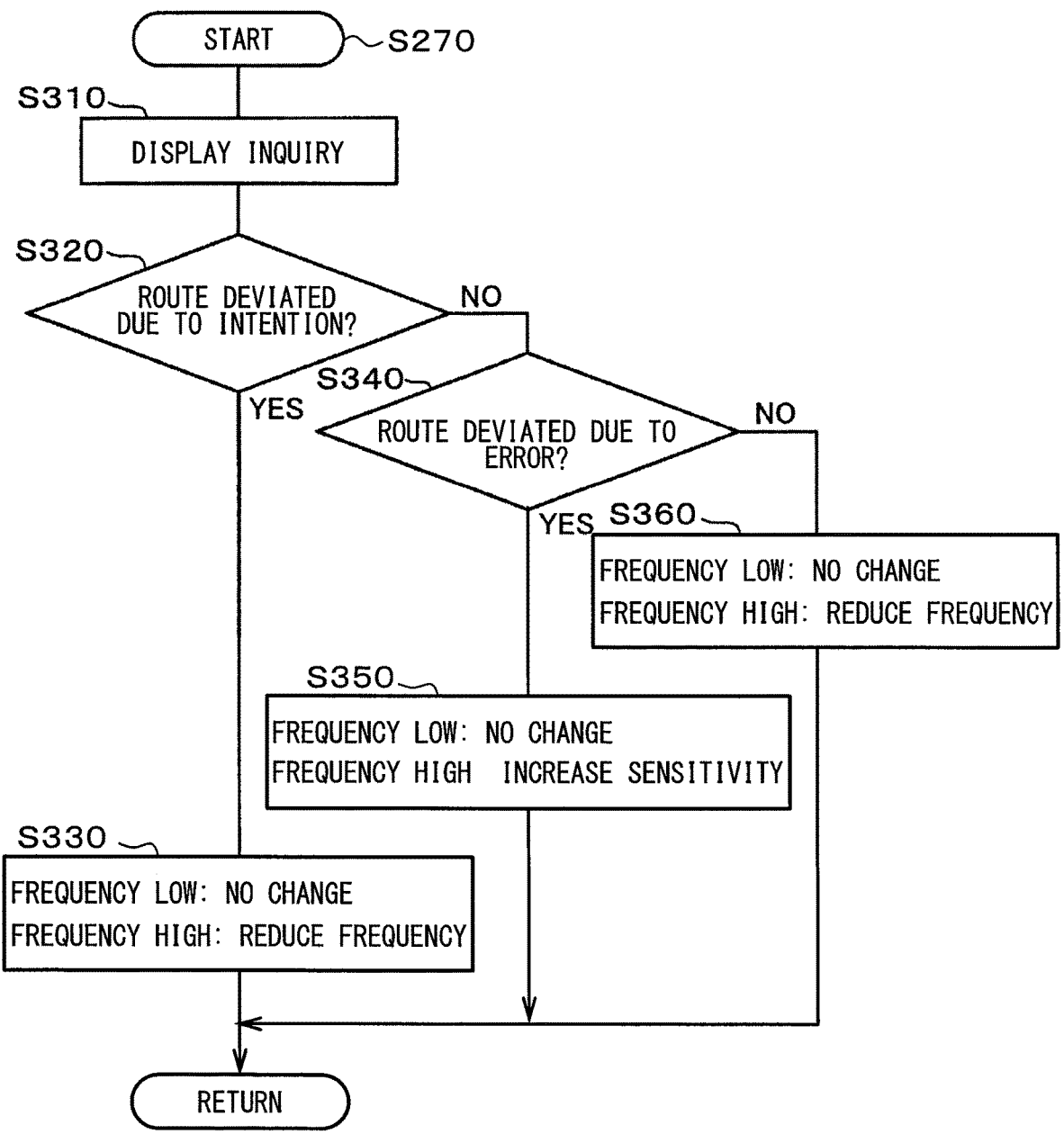
FIG. 5 is a flowchart of control of issuing an inquiry to a driver about a cause of discomfort of emotion.

The following will describe the control contents of S270 of FIG. 4, that is, a specific control of the process of inquiring the driver about the cause of discomfort in the emotion with reference to the flowchart of FIG. 5. This control is performed to confirm the driver's intention in cases that the change in the driver's brain activity or line of sight is small when the vehicle deviates from the calculated route so that the driver's intention cannot be determined.

First, in S310 of FIG. 5, the HMI controller 9 drives and controls the display and sound output unit 7 to display an inquiry screen on the display. This screen illustrates options such as a first option indicating that the route is deviated by the intention of the driver, a second option indicating that the route is deviated by no intention of the driver (that is, due to a driving error), and a third option indicating cancellation of the answer.

Subsequently, the process proceeds to S320, where the HMI controller 9 determines whether the driver's answer corresponds to the route deviation due to the intention of the driver. Here, when it is determined that the route is deviated by the intention of the driver (YES), the process proceeds to S330, where the HMI controller 9 stores data indicating that the driver's answer corresponds to the route deviation due to the intention of the driver. And, when the frequency of inquiring the driver about the intention is low, the threshold for determining the driver's intention is maintained unchanged. In contrast, when the frequently of inquiring the driver about the intention is high, the threshold for determining the driver's intention is changed to reduce the frequency of the inquiry. As a result, the present control is ended, and the process returns to S280 in FIG. 4.

In S320, when the driver's answer does not correspond to the route deviation due to the intention of the driver (NO), the process proceeds to S340. In S340, the HMI controller 9 determines whether the driver's answer corresponds to the route deviation without any intention of the driver (i.e., due to a driving error). Here, when the driver's answer corresponds to the route deviation without any intention of the driver (YES), the process proceeds to S350, where the HMI controller 9 stores data indicating that the driver's answer corresponds to the route deviation without any intention of the driver. And, when the frequency of inquiring the driver about the intention is low, the threshold for determining the driver's intention is maintained unchanged. In contrast, when the frequency of inquiring the driver about the intention is high, the threshold value for determining the driver's intention is changed to increase the sensitivity, that is, to increase the frequency of the inquiry. The reason for changing the threshold in this way is that, there is a necessity of increasing the sensitivity of the emotion detection threshold according to the characteristic of the driver, i.e., drivers who have small emotional movements such as calmness or insensitivity. As a result, the present control is ended, and the process returns to S280 in FIG. 4.

Further, when the driver's answer does not correspond to the route deviation without any intention of the driver in S340 (NO), the process proceeds to S360. In S360, the HMI controller 9 stores the data indicating that there is no driver's answer or the inquiry screen is cancelled. And, when the frequency of inquiring the driver about the intention is low, the threshold for determining the driver's intention is maintained unchanged. In contrast, when the frequency of inquiring the driver about the intention, the threshold for determining the driver's intention is changed to reduce the frequency of the inquiry. As a result, the present control is ended, and the process returns to S280 in FIG. 4.

Figure 6:
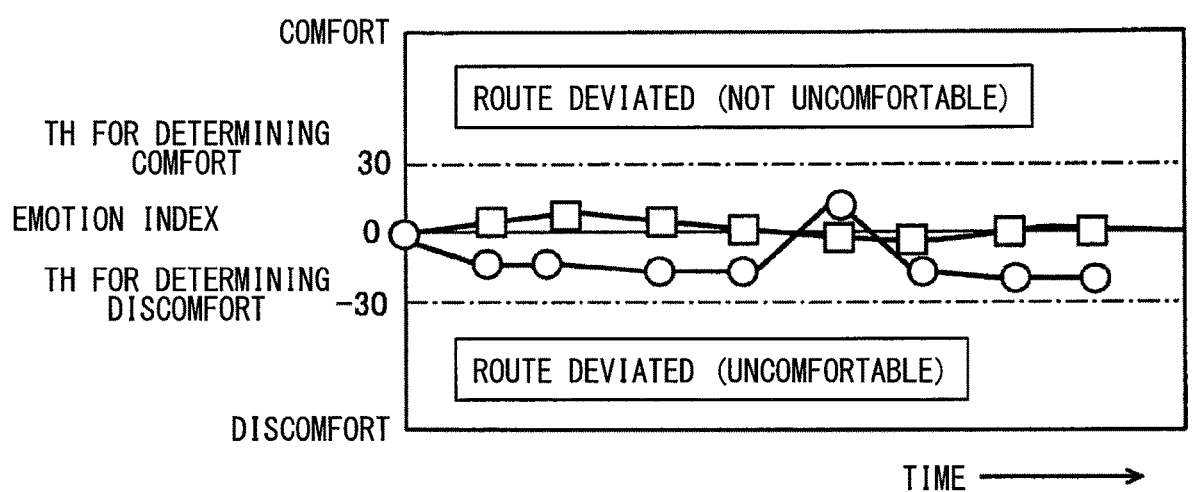
FIG. 6 is a characteristic diagram showing changes in emotion index.

Here, the relationship among the detected values of emotion index, the threshold value (TH) of determining comfort, and the threshold value (TH) of determining discomfort is shown in FIG. 6. In FIG. 6, the threshold value of determining comfort is "30" and the threshold value of determining discomfort is "−30". FIG. 6 shows the case where the change in the driver's emotion is small. Note that in S350 of FIG. 5, the control is performed to change both the threshold value of determining comfort and the threshold value of determining discomfort.

Figures 7, 8:
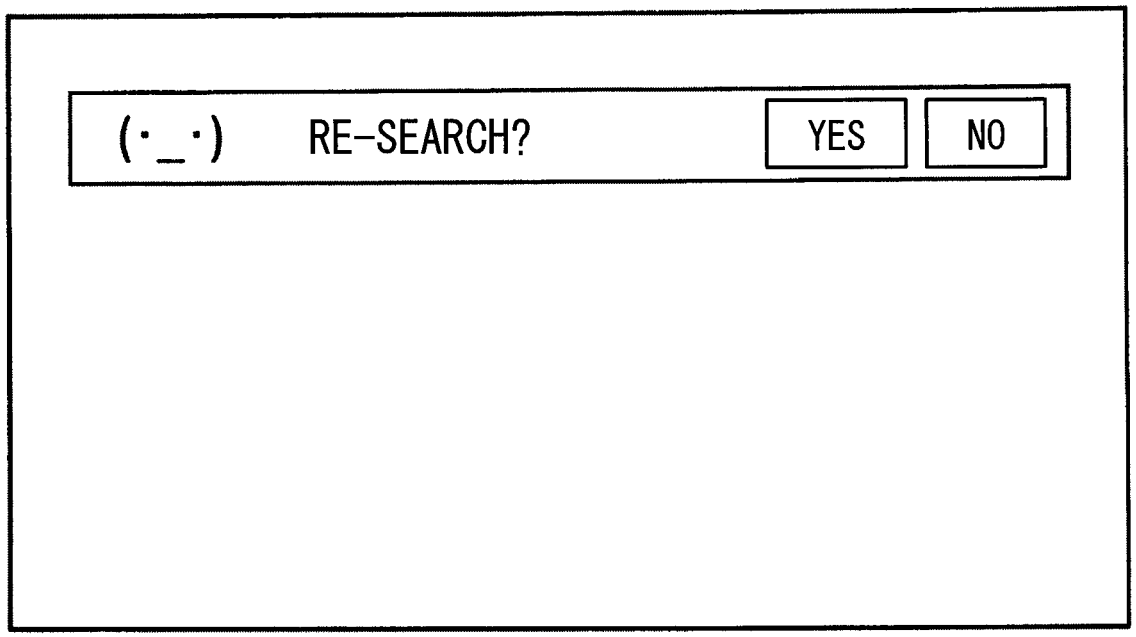
FIG. 7 is a diagram showing an example of an inquiry screen.
FIG. 8 is a diagram showing an example of a pictogram representing an emotion index.

Further, in the present embodiment, it is preferable that the driver be inquired of "Do you want to re-search the route?" when the vehicle deviates from the route. In this case, as shown in FIG. 7, it is preferable to display the detected emotion index in pictorial characters (i.e., pictograms) on the inquiry screen. The pictograms representing emotion indexes are prepared to include three types of pictograms shown in FIG. 8. In FIG. 8, the pictogram (a) indicates an emotion of comfort (for example, with confidence); the pictogram (b) indicates an emotion of a normality (for example, neither comfort nor discomfort); the pictogram (c) indicates an emotion of discomfort (for example, anxiety or concern). In displaying the pictogram, even if the detected emotion index does not exceed the threshold of determining comfort or discomfort, the pictogram of the emotion may be displayed if it is close to the threshold.

Figure 9:
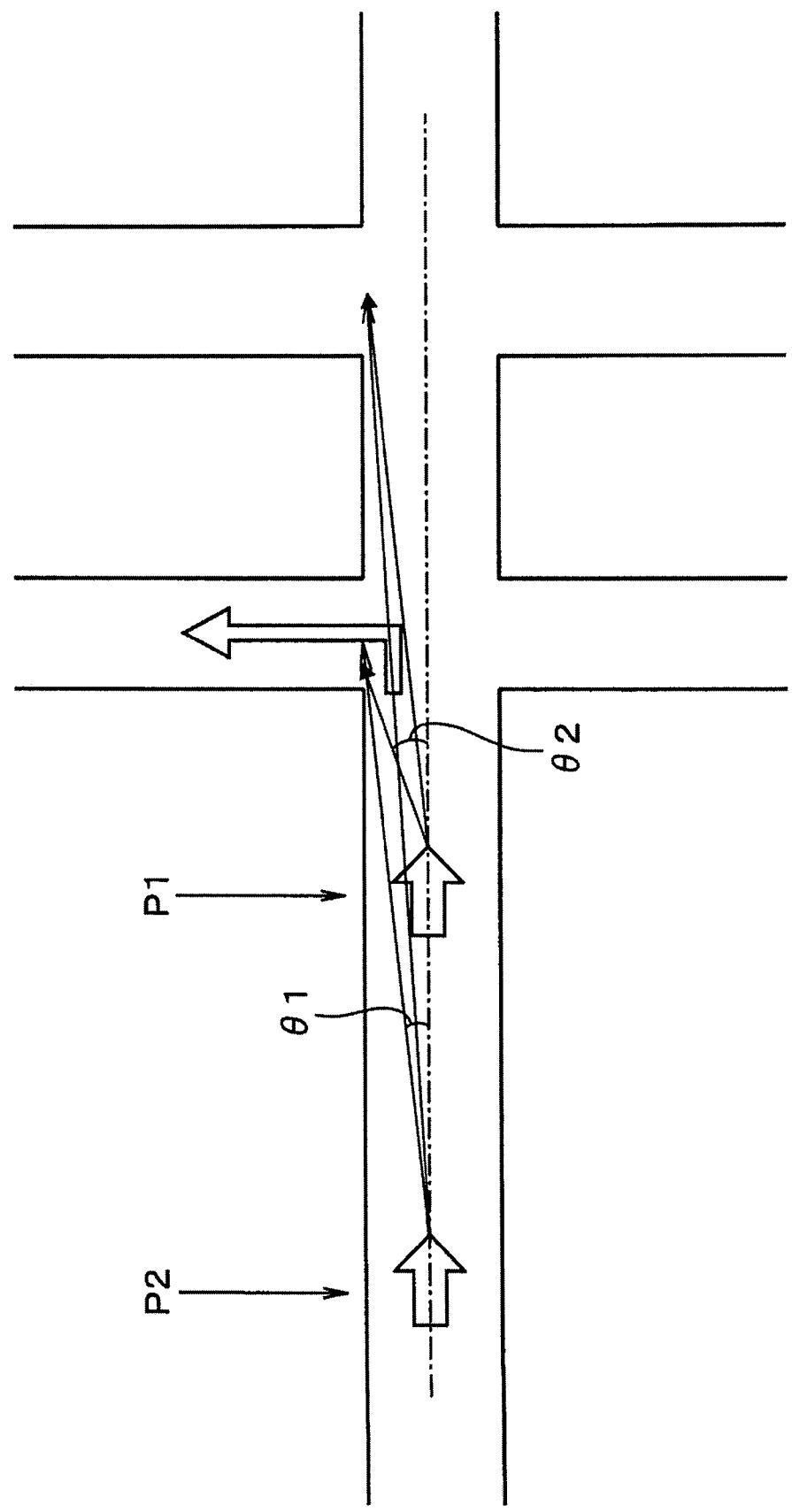
FIG. 9 is a diagram for explaining a specific example of notification control.

The following will describe a specific example of notification control below. With reference to FIG. 9, suppose a case that in a place with which the driver is unfamiliar, there are two adjacent intersections ahead, and the driver does not know which of the two intersections he will turn. In such a case, if there is no speech guidance, the driver becomes uneasy and looks around unstably. This is measured by the line-of-sight detection unit 3, and it is determined that the driver is looking around unstably (for example, S110 in FIG. 3).

In this case, in order to confirm the intersections, the driver takes an action that alternately sees two forward intersections (i.e., the driver takes an action of looking around unstably); this results in increasing the deviation of the line of sight (for example, the angle θ2). In addition, the driver gazes at the screen of the in-vehicle display (for example, the screen of the navigation unit) to check at which intersection the vehicle turns. In addition, the driver becomes anxious when the driver does not know the intersection where the vehicle turns, and the driver looks around (for example, S120 in FIG. 3). At that time, the brain activity of the driver is measured by the brain activity detection unit 2 and it is determined that there is anxiety. In the case of FIG. 9, the above two determination results are outputted at the position P1. Then, based on these two determination results, notification is performed at the position P1 (for example, S150 in FIG. 3). Note that in FIG. 9, at the position P2 ahead of the position P1, the deviation (for example, the angle θ1) of the line of sight is small, and the notification is not performed because the determination of looking around is not made affirmatively.

Now, as the anxiety is detected by the brain activity detection unit 2 and the looking-around determination is made affirmatively by the line-of-sight detection unit 3, the notification is performed at the position P1 near the intersection in FIG. 9. In this case, a driver unfamiliar with the place will be instructed to turn immediately at the nearest intersection, so the driver will perform a sharp steering manipulation. As a result, the driver has a sense of dissatisfaction that the notification by the HMI controller 9 should have been made earlier. This driver's dissatisfaction is grasped by the brain activity detection unit 2 measuring the driver's brain activity after the notification is performed (for example, S130 of FIG. 3). Then, when dissatisfaction or discomfort of the driver is detected by the measurement of the brain activity, the notification condition is changed (for example, S260 in FIG. 4).

In the present embodiment, the driver's dissatisfaction or discomfort can be grasped at one time, enabling the change of the notification condition appropriately. For instance, when the vehicle approaches, at the next time, a road configuration where two adjacent intersections ahead are present in a place with which the driver is unfamiliar, a notification can be performed several tens meters before, regardless of the result of the line-of-sight detection. As a result, in the case of FIG. 9, since the notification may be performed earlier at the position P2, the driver can perform the steering manipulation with a margin.

Further, in the present embodiment, whether a place where the driver travels is a place with which the driver is unfamiliar is recorded in a memory so as to be associated with the travel history of the driver's vehicle, and the anxiety value at the time of driving this place. Since the anxiety value is different for each driver, the average value of feeling anxiety for several drivers is used as a threshold value. While traveling, a place where the anxiety value is greater than a threshold value by a predetermined value is defined as a place with which the driver is unfamiliar.

Further, in the present embodiment, when there is not any option which the driver intends to answer, the driver's speech may be recorded. Such a speech is subjected to the speech recognition processing and is converted into text data to be recorded in a memory. The recorded text data may be searched for, using a keyword for estimating feeling or the like to estimate the driver's feeling or emotion. Then, based on the estimated driver's feeling, whether to need to change the notification condition may be preferably determined.

The following will describe operations of the HMI controller 9 and the brain activity detection unit 2 (that is, control contents of each determination process of S230 and S250 in FIG. 4) with reference to FIG. 10. FIG. 10 is a sequence diagram of controls of the HMI controller 9 and the brain activity detection unit 2.

First, when the power supply of the vehicle (i.e., the ignition switch) is turned on, measurement of brain activity of the driver is started by the brain activity detection unit 2 as shown in S410 in FIG. 10. As for the brain activity of the driver, the activity of each region in the brain is measured at a predetermined cycle by a plurality of brain activity sensors placed near the head, and the data is sequentially stored. Then, the process proceeds to S420, where the brain activity detection unit 2 analyzes the measured data, and determines the presence or absence of the deviation from the normal state. Here, if there is no deviation from the normal state (NO), the process returns to S410.

In S420, when there is a deviation from the normal state (YES), the process proceeds to S430, where the brain activity detection unit 2 estimates the driver's emotion (i.e., intention) using the determination data of deviation pattern. Then, the brain activity detection unit 2 transmits the result, that is, data indicating that the brain activity pattern deviates from the normal range, and the measured brain activity data to the HMI controller 9.

In contrast, when detecting that an event for confirming the driver's intention has occurred in S510 of the control by the HMI controller 9, the HMI controller 9 transmits a request for confirming whether or not the brain activity deviates from the normal range to the brain activity detection unit 2.

Thereafter, in S520, the HMI controller 9 receives brain activity data from the brain activity detection unit 2. Then, the process proceeds to S530, where the HMI controller 9 investigates the cause of the driver's brain excitation based on the received brain excitation data. Subsequently, the process proceeds to step S540. In S540, the HMI controller 9 searches for the cause of the driver's brain excitation in an inside of the vehicle such as manipulation by the driver, or the operation of the devices, by referring to time information of brain excitation data, and comparing it with data such as driver's driving manipulation data or driver's line-of-sight movement data. In this case, in S440 of the control by the brain activity detection unit 2, the brain activity detection unit 2 sets the timing and period for determining the driver's intention based on the start time of the route deviation for searching for the cause, determines what pattern of brain activity has occurred, and transmits the determined brain activity data to the HMI controller 9.

Next, the process proceeds to S550, where the HMI controller 9 determines whether the cause of the driver's brain excitation is in an inside of the vehicle. Here, when the cause is in an inside of the vehicle (YES), the process proceeds to S560, where the HMI controller 9 stores data indicating that the cause is in an inside of the vehicle in the memory. When the cause is not in an inside of the vehicle In S550 (NO), the process proceeds to S570. In S570, the HMI controller 9 searches for the cause in an outside of the vehicle by referring to the camera image for capturing images in an outside of the vehicle or the action history of the driver's line-of-sight direction.

Subsequently, the process proceeds to S580, where the HMI controller 9 determines whether the cause of the driver's brain activity is in an outside of the vehicle (for example, recognition of danger on a road). Here, when the cause is in an outside of the vehicle (YES), the process proceeds to S590, where the HMI controller 9 stores data indicating that the cause is in an outside of the vehicle in the memory. When the cause is not in an outside of the vehicle in S580 (NO), the process proceeds to S600, where the HMI controller 9 stores in the memory data indicating that the cause is unknown (whether the cause is in an inside or an outside is unknown or undetermined).

Then, in S610, the HMI controller 9 requests the brain activity detection unit 2 to transmit additional brain activity data if the brain activity data to be recorded is insufficient. In response to this request, in S450, the brain activity detection unit 2 transmits additional brain activity data (i.e., missing data) to the HMI controller 9.

Thereafter, the process proceeds to S620, where the HMI controller 9 stores in the memory (i) brain excitation data indicating that the driver's intention (i.e., brain excitation pattern) is out of the normal range, and (ii) data indicating that the cause generating the driver's brain excitation is in an inside of the vehicle, in an outside of the vehicle, or unknown (for example, information such as location and time is added) to be added to the brain excitation data.

In this embodiment, the brain activity data recorded as described above is used to optimize each operation of various in-vehicle devices to match the driver's intention. That is, the present embodiment checks an operation of an in-vehicle device manipulated by the driver or an automatic operation of the in-vehicle device before the driver felt uncomfortable, thereby finding a trigger for improving such an operation.

Figure 11:
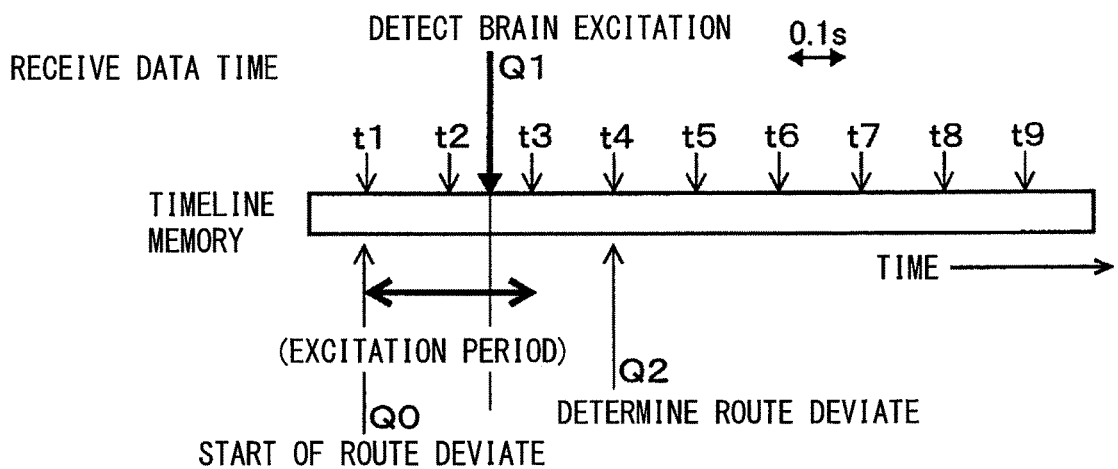
FIG. 11 is a diagram schematically showing a detection procedure of brain excitation.

FIG. 11 is a diagram schematically showing a detection procedure for detecting brain excitation. It is noted that the brain activity detection unit 2 may be achieved as a controller to provide a plurality of functions, like the HMI controller 9. Such a controller is configured by including (i) hardware circuits (circuitry), or (ii) a microcomputer, or (iii) a combination of the hardware circuits and the microcomputer, with related apparatuses such as sensors or detectors. In such a case, the process of detecting brain excitation may be executed by the brain activity detection unit 2, for instance, by using a CPU included in a microcomputer. In contrast, when the brain activity detection unit 2 is configured only by sensors that measure brain activity, for example, the HMI controller 9 is configured to execute processing for collecting and analyzing measurement data of brain activity and detecting brain excitation.

In the measurement of brain activity, a plurality of sensors are in close contact with each part of the head (for example, the forehead, the vicinity of the ear, the top of the head, etc.), and the in-brain state is repeatedly measured at a rate of about once every 100 milliseconds. In FIG. 11, t1, t2, t3, . . . indicate the time for each measurement (i.e., measurement time). The further to the right of the timeline, the newer the measurement time is. The time-line memory stores the time and the measured value of brain activity as a pair; by specifying a continuous period of time, the measurement data in the continuous period of time may be acquired collectively and efficiently. Further, a position Q1 shown as "DETECT BRAIN EXCITATION" in FIG. 11 indicates a point of time at which the brain activity transitions into brain excitation after measuring the brain activity data at time t2.

In contrast, a position Q2 (i.e., time t4) shown in FIG. 11 as "DETERMINE ROUTE DEVIATE" indicates a point of time at which it is determined that the vehicle deviates from the set guidance route based on the measurement of traveling state of the vehicle. To determine the deviation from the route of the vehicle, various calculations are necessary, such as current position calculation, travel route calculation, and determination of traveling road position; therefore, a time delay occurs before determining the deviation from the route. When the route deviation is determined, (i) the position at which the route deviation started and (ii) the route deviation start time are obtained from the calculation result. In FIG. 11, a position Q0 (i.e., time t1) is a position at which the route deviation started.

In order to determine the movement of the driver's emotion, the time (point of time) at which the driver's emotion movement is likely to occur is traced back to a time (for example, the route start time t1) before the time t4 at which the route deviation is determined. Then, the tendency of time-based change in the driver's emotion movement is used to set a time range corresponding to the driver's emotion movement (that is, the emotion excitation time) and analyze the emotion movement (emotion index).

Figure 12:
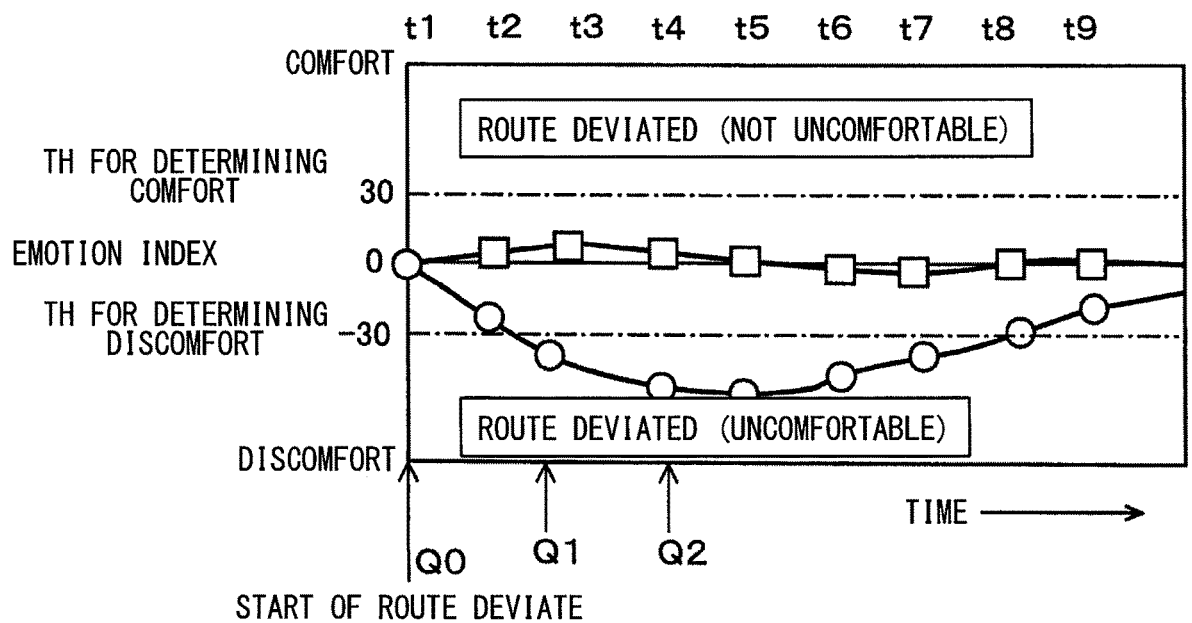
FIG. 12 is a characteristic diagram showing changes in emotion index.

FIG. 12 is a graph of time-based change in comfort and discomfort as an emotion index. The vertical axis in FIG. 12 is a value representing comfort and discomfort, and the horizontal axis is time. Measurement values (i.e., data) of a plurality of sensors for measuring brain activity are sent to the CPU of the brain activity detection unit 2. These measurement data are summarized as changes in each region of the brain, and are compared with measurement data of each region of the brain measured last time. Then, the degree of the change is replaced with a change of the driver's various emotions (for example, emotions such as comfort and discomfort) using a data conversion formula. As a result, the time-based change in the emotion is acquired.

Here, a threshold value is provided to distinguish between the normal state and the brain excitation state. When the time exceeding the threshold value becomes equal to or greater than the set time, it may be determined that the driver's brain excitation has occurred. In FIG. 12, a circle indicates that an uncomfortable situation has occurred, and a square indicates that it is in a normal state. As shown in FIG. 12, several points of circle marked below the discomfort determination threshold value "−30" are measured or observed when the route deviation is determined; thus, it is determined that the driver felt the route deviation uncomfortable when the route deviation occurs.

Furthermore, FIG. 11 illustrates a situation where, "DETECT BRAIN EXCITATION" is detected after time t2 and an event of the start of the route deviation occurs at time t1. Such a situation allows the determination that the driver's brain excitation may have occurred due to the start of the route deviation. Note that changes in brain excitation depend on the driver's emotional characteristics. In order to investigate the cause after determining a detection of a brain excitation, the measurement values of the brain excitation are analyzed during a period of time corresponding to the driver's emotional characteristics (e.g., an excitation period of time of the brain excitation (i.e., emotion excitation period of time)), as described above. In this case, if depending on the emotion, the emotion excitation period of time is set according to the detected emotion. For example, when emotion is happy, emotion excitation period of time is set to be short; when sad, emotion excitation period of time is set to be long.

Moreover, if there are possibilities that the operation of the in-vehicle device or the driver's driving manipulation may cause the brain excitation of the driver other than the route deviation, the cause of the brain excitation need to be narrowed down from such possibilities. In this case, the driver's emotion is determined based on the measurement patterns or the time-based change in the detected sensor values by a plurality of sensors of the brain activity detection unit 2. For example, what kind of emotion the driver has may be determined based on the positions of the sensors and the magnitudes of the brain excitation detected by the sensors.

In the present embodiment of the above configuration, the state of the driver's driving manipulation and the driver's emotion are measured; the measured results are used for determining the driver's intention accurately and quickly. This suppresses the notification of a route deviation from being issued when the driver intentionally deviates from the route. The driver is thus suppressed from receiving an uncomfortable notification; this can achieve a configuration that is easy to use and is comfortable.

It is noted that, the above embodiment describes the example configurations of the following several units including the brain activity detection unit 2, the line-of-sight detection unit 3, the vehicle manipulation measurement unit 4, the vehicle position measurement unit 5, and the navigation unit 6, the display and sound output unit 7, and the manipulation unit 8, in addition to the HMI controller 9. Furthermore, other example configurations of such a unit may be additionally employed. Thus, the example configurations of such a unit may be summarized as below.

That is, each unit 2 to 8 may be also achieved as a controller, like the HMI controller 9, with functions of related apparatuses such as sensors or detectors. Such a controller including the HMI controller 9 may be combined with another controller, or be divided into several controllers (i.e., a controller may be provided as at least one controller).

Such at least one controller provides a plurality of functions and may include sections to provide the respective functions. In addition, a flowchart or sequence executed by a controller includes sections, e.g., each represented as S10, S20, or the like executed by the HMI controller 9 in the above embodiment. Several sections may be combined into a single section; one section may be divided into several sections. Each section may be also referred to or achieved as a unit, module, device, detector, or the like.

Furthermore, (i) an individual one of the sections or the like included in at least one controller, or (ii) an individual controller of the at least one controller may be achieved by using or by including (i) at least one hardware circuit (i.e., circuitry) including analog circuit and/or digital circuit, or (ii) at least one processing unit (such as a CPU in a computer) along with memory storing instructions (such as a non-transitory tangible computer-readable storage medium storing instructions of program executed by the CPU), or (iii) a combination of the at least one hardware circuit and the at least one processing unit along with memory storing instructions, to thereby provide the functions.

In addition, at least one control circuit may be provided by including or by being accompanied by a storage, an interface communicating with an external apparatus, and an internal communication line connecting the foregoing components to each other, with or without a function of a related apparatus such as a sensor or detector.

For reference to further explain features of the present disclosure, the description is added as follows.

In some navigation apparatuses performing a route guidance, if a vehicle deviates from the guidance route, an audio guidance is outputted such as "deviated from the route, perform re-route calculation". However, the driver may intentionally select a different route that is deviated from the guidance route (that is, a route that is incorrect when viewed from the navigation apparatus). In such a case, if the audio guidance is repeated, the driver feels bothersome or uncomfortable.

To cope with the case, the detection of a behavior pattern or preference of the driver (i.e., the user) may be effective in controlling to suppress output of the audio guidance. In a certain apparatus, a driver's behavior pattern and preference are detected.

In the above certain apparatus, an intention determination unit determines whether a travel route of an information processing apparatus is selected intentionally by the driver based on the relationship between the travel route and the guidance route provided by a route search unit. When it is determined that the travel route is selected intentionally by the driver, a preference determination unit determines the driver's preference based on (i) the history such as information acquired by sensors and (ii) the preference and action rule.

The above certain apparatus learns information that the driver has intentionally moved and accumulate such information to thereby determine the driver's preference. In order to increase the accuracy of the driver's preference, a large number of learning opportunities or times is thus required, which has a disadvantage in taking a long time. In addition, the preference of an individual person (i.e., the driver) fluctuates due to various conditions of the driver. If the preference of the driver is determined only by the travel history as in the certain apparatus, the determination accuracy of the preference of the driver may be lowered.

In some embodiments of the present disclosure, a vehicular notification apparatus measures (i) a state of a driver's driving manipulation and (ii) a driver's emotion, thereby determining the driver's intention accurately and promptly so as to suppress uncomfortable notification.

Embodiments of the present disclosure described herein are set forth in the following clauses.

According to an embodiment of the present disclosure, a vehicular notification apparatus may be provided as including a line-of-sight detector configured to detect a line of sight of a driver of a vehicle to provide a line-of-sight detection result; a brain activity detector configured to detect a brain activity of the driver to provide a brain activity detection result; and at least one controller connected with the line-of-sight detector and the brain activity detector via a communication line. The controller is configured (i) as a notification determination section to determine whether a notification-required condition occurs; (ii) as an emotion detector section to detect an emotion of the driver based on the line-of-sight detection result and the brain activity detection result, and (iii) as a notification control section to perform control so as to suppress notification in response to that the detected emotion of the driver is uncomfortable.

Further according an optional embodiment of the above embodiment, the at least one controller may be configured to include (i) circuitry, and/or (ii) a processing unit along with memory storing instructions.

While the present disclosure has been described with reference to the embodiment thereof, it is to be understood that the present disclosure is not limited to the embodiment and its configuration. The present disclosure is intended to cover various modification and equivalents. In addition, while the various elements are shown in various combinations and configurations, which are exemplary, other combinations and configurations, including more, less or only a single element, are also within the spirit and scope of the present disclosure.

What is claimed is:

1. A vehicular notification apparatus, comprising:
a line-of-sight detector configured to detect a line of sight of a driver of a vehicle to provide a line-of-sight detection result;
a brain activity detector configured to detect a brain activity of the driver to provide a brain activity detection result; and
at least one controller connected with the line-of-sight detector and the brain activity detector via a communication line,
the controller configured
(i) to determine whether a notification-required condition occurs;
(ii) to detect an emotion of the driver based on the line-of-sight detection result and the brain activity detection result, and
(iii) to perform control so as to suppress notification in response to that the detected emotion of the driver is uncomfortable,
wherein the controller is configured to detect the emotion of the driver in response to that a notification is performed,
wherein in response to that the detected emotion is uncomfortable and a cause of being uncomfortable is undetermined, the controller is configured to issue an inquiry about the cause of being uncomfortable to the driver,
wherein in response to issuing the inquiry and then receiving an answer indicating that the cause of being uncomfortable is an intention of the driver, the controller is configured to reduce a frequency of inquiries if the frequency of inquiries is determined to be higher than a threshold value.

2. A vehicular notification apparatus, comprising:
a line-of-sight detector configured to detect a line of sight of a driver of a vehicle to provide a line-of-sight detection result;
a brain activity detector configured to detect a brain activity of the driver to provide a brain activity detection result; and
at least one controller connected with the line-of-sight detector and the brain activity detector via a communication line,
the controller configured
(i) to determine whether a notification-required condition occurs;
(ii) to detect an emotion of the driver based on the line-of-sight detection result and the brain activity detection result, and
(iii) to perform control so as to suppress notification in response to that the detected emotion of the driver is uncomfortable,
wherein the controller is configured to detect the emotion of the driver in response to that a notification is performed,
wherein in response to that the detected emotion is uncomfortable and a cause of being uncomfortable is undetermined, the controller is configured to issue an inquiry about the cause of being uncomfortable to the driver,
wherein in response to issuing the inquiry and then receiving an answer indicating that the cause of being uncomfortable is an error in driving by the driver, the controller is configured to change a threshold value to increase a sensitivity.

3. A vehicular notification apparatus, comprising:
a line-of-sight detector configured to detect a line of sight of a driver of a vehicle to provide a line-of-sight detection result;
a brain activity detector configured to detect a brain activity of the driver to provide a brain activity detection result; and
at least one controller connected with the line-of-sight detector and the brain activity detector via a communication line,
the controller configured
(i) to determine whether a notification-required condition occurs;
(ii) to detect an emotion of the driver based on the line-of-sight detection result and the brain activity detection result, and
(iii) to perform control so as to suppress notification in response to that the detected emotion of the driver is uncomfortable,
wherein the controller is configured to detect the emotion of the driver in response to that a notification is performed,
wherein in response to that the detected emotion is uncomfortable and a cause of being uncomfortable is undetermined, the controller is configured to issue an inquiry about the cause of being uncomfortable to the driver,
wherein in response to issuing the inquiry and then failing to receive an answer, the controller is configured to reduce a frequency of inquiries if the frequency of inquiries is determined to be higher than a threshold value.

4. The vehicular notification apparatus according to claim 1, further comprising:
a notification device connected with a display, the notification device being configured to display a notification message and a pictogram corresponding to the detected emotion of the driver on the display.

5. The vehicular notification apparatus according to claim 2, further comprising:
a notification device connected with a display, the notification device being configured to display a notification message and a pictogram corresponding to the detected emotion of the driver on the display.

6. The vehicular notification apparatus according to claim 3, further comprising:
a notification device connected with a display, the notification device being configured to display a notification message and a pictogram corresponding to the detected emotion of the driver on the display.

* * * * *